United States Patent [19]

Kraus et al.

[11] Patent Number: 5,780,638
[45] Date of Patent: Jul. 14, 1998

[54] PROCESS FOR THE PREPARATION OF 5-HYDROXYMETHYLTHIAZOLE

[75] Inventors: Helmut Kraus, Odenthal; Helmut Fiege, Leverkusen, both of Germany

[73] Assignee: Bayer Aktiengesellschaft, Leverkusen, Germany

[21] Appl. No.: 762,625

[22] Filed: Dec. 9, 1996

[30] Foreign Application Priority Data

Dec. 18, 1995 [DE] Germany ............... 195 47 076.1

[51] Int. Cl.$^6$ ............................................. C07D 277/24
[52] U.S. Cl. ............................... 548/203; 548/200
[58] Field of Search ............................. 548/203, 200

[56] References Cited

FOREIGN PATENT DOCUMENTS 0486948  5/1992  European Pat. Off. .

OTHER PUBLICATIONS

Kerdesky, Synthetic Communication, 25(17), 2639, 1995.
Lancaster Catalog pp. 190–191, 1995.
Potts Comprehensive Heterocyclic Chemistry, vol. 6, p. 295, 1984.
von H. Erlenmeyer, et al., 245. Zur Kenntnis des α[Thiazolyl–(5)]–pyrrolidins, Helv. Chim.Acts., 29, (1946).
van S. Fallab, 27. Über Thiazolyl–(5)–carbinol, Helv. Chim. Acts., 35, 215, (1952).

*Primary Examiner*—Robert Gerstl
*Attorney, Agent, or Firm*—Sprung Kramer Schaefer & Briscoe

[57] ABSTRACT

5-Hydroxymethylthiazole is prepared in an improved manner by reducing 5-formylthiazole using a borane compound. Particularly advantageous in this case is the use of 5-formylthiazole which has been obtained by reaction of a 2-halomalonaldehyde compound with thioformamide in the presence of less than 5% by weight of water (based on the reaction mixture).

11 Claims, No Drawings

PROCESS FOR THE PREPARATION OF 5-HYDROXYMETHYLTHIAZOLE

5-Hydroxymethylthiazole is an intermediate for the preparation of medicaments (see, for example, J. Med. Chem. 16, 978 (1964)).

It is known that 5-hydroxymethylthiazole can be prepared by reducing 5-carbethoxythiazole with lithium aluminum hydride.

According to Helv. Chim. Acta 35, 215 (1952), in the customary procedure 5-hydroxymethylthiazole is obtained in this way only in very low yield. On restriction of the addition of water in the work-up to a minimum and immediate neutralization of the resulting lithium hydroxide with carbon dioxide, the yield can be brought to 70 to 80%. According to Example 80 B of EP-A2 0 486 948, 5-hydroxymethylthiazole is obtained by reduction of 5-carbethoxythiazole using lithium aluminum hydride in 44% crude yield. 5-Hydroxymethylthiazole is thus not obtainable in good yields in a simple and highly reproducible manner. Furthermore, in this process working with lithium aluminum hydride requires expensive safety measures, which are very disadvantageous, in particular with a procedure on the industrial scale. Additionally, the 5-carbethoxythiazole needed for this process as a starting material is only accessible by processes which produce it in very low yields. Thus, according to Example 80 A of EP-A2 0 486 948 5-carbethoxythiazole is obtained in a yield of only 33% and according to Helv. Chim. Acta 29 1946 (1946), of only 37% (calculated on the weight details given there).

The two-stage preparation of 5-hydroxymethylthiazole according to the prior art can thus at the very best be carried out in total yields of around 30%.

There is therefore still the need for a process with which in a manner which is simple, reproducible and requires less safety expenditure, 5-hydroxymethylthiazole is accessible in good yields.

A process for the preparation of 5-hydroxymethylthiazole has now been found, which comprises reducing 5-formylthiazole using a borane compound.

Possible borane compounds are, for example, aminoboranes and borohydrides. The aminoboranes may correspond, for example, to the formula (I)

$$BH_3-NR^1R^2R^3 \qquad (I),$$

in which $R^1$, $R^2$ and $R^3$ are identical or different and each represent hydrogen, $C_1-C_6$-alkyl or phenyl or $R^1$, $R^2$ and $R^3$, together with the nitrogen atom to which they are bonded, represent a nitrogen-containing heterocycle.

Preferably, $R^1$, $R^2$ and $R^3$ are identical or different and represent hydrogen or $C_1-C_4$-allyl or $R^1$, $R^2$ and $R^3$, together with the nitrogen atom to which they are bonded, represent pyridine, morpholine or pyrazole. Particularly preferred meanings of the $NR^1R^2R^3$ radical are: ammonia, dimethylamine, trimethylamine, diethylamine, triethylamine, pyridine and morpholine.

Possible borohydrides are, for example, those of the formula (II)

$$MBH_xY_{4-x} \qquad (II),$$

in which

M represents an alkali metal or one equivalent of an alkaline earth metal,

Y represents cyano, $C_1-C_4$-alkoxy or $C_1-C_4$-carboxy and x represents 2, 3 or 4.

Preferably, M represents sodium or potassium, Y represents cyano and x represents 3 or 4. Particularly preferred compounds of the formula (II) are: sodium tetrahydroborate, potassium tetrahydroborate and sodium trihydromonocyanoborate.

Based on 1 mol of 5-formylthiazole for example, 0.25 to 3 mol of a borane compound can be employed. Preferably, this amount is in the range 0.4 to 2 mol.

Suitable temperatures for the reduction according to the invention are, for example, those in the range 0° to 60° C. Preferred temperatures are in the range 20° to 40° C.

The respective borane compound can be added as such, e.g. in solid, liquid or molten form, or dissolved in a solvent. Suitable solvents are, for example, water, ethers such as tetrahydrofuran, dioxane and diglyme, alcohols such as methanol, ethanol, and isopropanol, amines such as diusopropylamine and pyridine, mixtures of these solvents and two-phase systems, e.g. of methylene chloride and water. Also, independently of the addition of the respective borane compound, the process according to the invention can be carried out in the presence of such solvents.

Before addition of the borane compound, the reaction mixture may optionally be rendered alkaline using alkali metal hydroxide. This is advantageous, for example, if tetrahydroborates are employed as boron compounds.

In the process according to the invention, 5-formylthiazole of any desired origin can be employed (see, for example, EP 395 174, DE 1 182 234 and J. Med. Chem. 12, 374 (1968)). Preferably, 5-formylthiazole is employed which has been obtained by reaction of a 2-halomalonaldehyde compound of the formula

in which

R represents hydrogen, an alkali metal or one equivalent of an alkaline earth metal and X is fluorine, chlorine, bromine or iodine, with thioformamide in the presence of less than 5% by weight of water (based on the reaction mixture). If appropriate, this preparation of 5-formylthiazole can be carried out in the presence of solvents, e.g. ethers, in the presence of carboxylic acids, e.g. formic or acetic acid, and if appropriate in the presence of buffering alkali metal salts at, for example, −20° to +80° C. The 5-formylthiazole prepared from a 2-halomalonaldehyde compound of the formula (III) is particularly preferably employed in nonisolated form, e.g. in the form of the reaction mixture present after the reaction of the compound of the formula (III) with thioformamide. Such reaction mixtures may contain, for example, from 3 to 30% by weight of 5-formylthiazole and additionally, for example, polymers and phosphorus compounds resulting from the $P_4S_{10}$ employed in the thioformamide preparation. The borane compound to be employed according to the invention can be added directly to reaction mixtures of this type and can thus be prepared in a one-pot process first 5-formylthiazole and then 5-hydroxymethylthiazole.

The reaction of compounds of the formula (III) with thioformamide in the presence of less than 5% by weight of water is the subject of a separate patent application.

The reaction mixture present after carrying out the process according to the invention can be worked up, for example, by concentrating it, treating the residue with water and optionally alkali metal hydroxide, then extracting with an extracting agent (optionally several times) and recovering the 5-hydroxymethylthiazole prepared from the extract by evaporating the solvent. If appropriate, it can be further purified by distillation.

Possible extracting agents are, for example, chloroalkanes and optionally chlorinated aromatics such as methylene chloride, dichloroethane, chlorobenzene and toluene.

The process according to the invention has the advantage that it permits the preparation of 5-hydroxymethylthiazole using, in comparison with lithium aluminum hydride, weaker reductants from the borane compounds class avoiding particularly expensive safety precautions. Starting from pure 5-formylthiazole, 5-hydroxymethylthiazole can thus be obtained in yields of, for example, 92 to 99% of theory. On the preferred use of 5-formylthiazole in the form of a crude reaction solution as it is obtained in the reaction of 2-halomalonaldehyde compounds of the formula (III) with thioformamide, yields in the range of 65 to 80% of theory can be achieved over both reaction stages (preparation of 5-formylthiazole and preparation of 5-hydroxymethylthiazole). These yields are more than twice as large as in the 2-stage preparation of 2-hydroxymethylthiazole via 5-carbethoxythiazole according to the prior art described at the outset.

EXAMPLES

Example 1

Preparation of a reaction mixture containing 5-formylthiazole which is particularly suitable as a starting material (not according to the invention).

50 g of dried sodium chloromalonaldehyde and 26.3 g of sodium formate were initially introduced into 400 ml of formic acid, 420 g of thioformamide solution (in the form of a crude, 6.5% strength by weight solution in tetrahydrofuran obtained on preparation thereof from formamide and $P_4S_{10}$) were added dropwise at 40° C. and after 1 hour at 60° C. the solid was filtered off. According to $^1$H-NMR, the reaction mixture then present contained 5-formylthiazole in an amount which corresponded to 79.7% of theory. The reaction mixture contained 1.3% by weight of water.

Example 2

4 g of molten dimethylaminoborane were added dropwise at 20° C. to 40% by weight of the solution obtained as in Example 1. The mixture was then concentrated on a rotary evaporator, treated with water and sodium hydroxide solution until a pH of 7 was achieved and extracted three times with 50 ml of methylene chloride each time. The extracts were combined and after concentrating again on a rotary evaporator 19.4 g of 5-hydroxymethylthiazole having a purity of 67.7 % by weight (=73.4% of theory, based on sodium chloromalonaldehyde) were obtained. By distillation in a bulb tube oven, a product of 96.1% purity was obtained at 120° C./0.5 mbar.

$^1$H-NMR (CDCl$_3$): 8.72 ppm (s, 1H), 7.71 ppm (s, 1H), 4.90 ppm (s, 2H), 3 to 4 ppm (bs, 1H).

Example 3

A solution of 3 g of sodium tetrahydroborate in 18 g of water was added dropwise at 20° C. to 40% by weight of the solution obtained as in Example 1, the mixture was concentrated on a rotary evaporator and a pH of 10 was established using sodium hydroxide solution. The mixture was extracted three times using 50 ml of methylene chloride each time, the extracts were combined and the methylene chloride was stripped off on a rotary evaporator. The residue which remained contained 5-hydroxymethylthiazole in an amount which corresponded to 69.7% of theory (based on sodium chloromalonaldehyde).

Example 4

The procedure was as in Example 2, but instead of dimethylaminoborane, a solution of 10.0 g of sodium trihydromonocyanoborate in 15 ml of tetrahydrofuran was added dropwise and the mixture was not treated with sodium hydroxide solution. The product present after the concentration of the combined extracts contained 5-hydroxymethylthiazole in an amount which corresponded to 75.0% of theory (based on sodium chloromalonaldehyde).

Example 5

The procedure was as in Example 2, but as the borane compound the corresponding amount of potassium tetrahydroborate in 15 ml of tetrahydrofuran was added dropwise. The product present after concentration of the extracts contained 5-hydroxymethylthiazole in an amount which corresponded to 67.3% of theory (based on sodium chloromalonaldehyde).

Example 6

A mixture of 20 ml of methylene chloride, 10 ml of water and 1.7 g of sodium tetrahydroborate was initially introduced and 10.5 g of 96.8% strength 5-formylthiazole (containing 2% formic acid and 0.5% formamide) were added dropwise at 20° C. After one hour, a pH of 1 was established using concentrated hydrochloric acid. Then a pH of 7 was established using 45% strength aqueous sodium hydroxide solution and then the phases were separated. The aqueous phase was extracted twice using 20 ml of methylene chloride each time and the combined methylene chloride phases were concentrated. The yield of 5-hydroxymethylthiazole was 97.7% of theory (based on 5-formylthiazole).

We claim:

1. A process for the preparation of 5-hydroxymethylthiazole, which comprises reacting a 2-halomalonaldehyde compound of the formula

(III)

in which

R represents hydrogen, an alkali metal or an equivalent of an alkaline earth metal and X is fluorine, chlorine, bromine or iodine, with thioformamide in the presence of less than 5% by weight of water to obtain 5-formylthiazole, reducing the 5-formylthiazole using a borane compound, wherein the borane compound employed is an aminoborane of the formula $$BH_3\text{—}NR^1R^2R^3 \qquad (I),$$

in which $R^1$, $R^2$ and $R^3$ are identical or different and each represent hydrogen, $C_1$–$C_{16}$-alkyl or phenyl or wherein the borane compound employed is a borohydride of the formula $$MBH_xY_{4-x} \quad (II),$$

in which

M represents an alkali metal or one equivalent of an alkali earth metal,

Y represents cyano, $C_1$–$C_4$-alkoxy or $C_1$–$C_4$-carboxy and x represents 2, or 3.

2. The process as claimed in claim 1, wherein 0.25 to 3 mol of a borane compound is employed relative to 1 mol of 5-formylthiazole.

3. The process as claimed in claim 1, wherein the reduction reaction is carried out at temperatures in the range 0° to 60° C.

4. The process as claimed in claim 1, wherein 5-formylthiazole is employed in the form of the reaction mixture present after the reaction of the compound of the formula (III) with thioformamide.

5. The process as claimed in claim 1, wherein the reaction mixture present after the reduction is worked up by concentrating it, treating the residue with water and optionally alkali metal hydroxide, then extracting with an extracting agent and recovering the 5-hydroxymethylthiazole prepared from the extract by evaporating the solvent.

6. The process as claimed in claim 1, wherein the borane compound employed is an aminoborane.

7. The process as claimed in claim 1, wherein the borane compound employed is a borohydride.

8. The process as claimed in claim 1, wherein the reduction of the 5-formylthiazole is conducted only in the water carried by the 5-formylthiazole reaction product.

9. The process as claimed in claim 1, wherein the aminoborane is used in molten form.

10. The process as claimed in claim 1, wherein the aminoborane is dimethylaminoborane.

11. The process as claimed in claim 1, wherein the borane is sodium trihydromonocyanoborate.

\* \* \* \* \*